United States Patent
Green

(10) Patent No.: US 8,562,907 B2
(45) Date of Patent: Oct. 22, 2013

(54) HAND SANITIZER

(75) Inventor: Bruce Green, Northampton (GB)

(73) Assignee: Tristel PLC, Snailwell, Newmarket (GB)

(*) Notice: Subject to any disclaimer, the term of this patent is extended or adjusted under 35 U.S.C. 154(b) by 0 days.

(21) Appl. No.: 13/818,731

(22) PCT Filed: Sep. 20, 2011

(86) PCT No.: PCT/GB2011/051768
§ 371 (c)(1),
(2), (4) Date: Apr. 23, 2013

(87) PCT Pub. No.: WO2012/042243
PCT Pub. Date: Apr. 5, 2012

(65) Prior Publication Data
US 2013/0202484 A1 Aug. 8, 2013

Related U.S. Application Data

(60) Provisional application No. 61/387,729, filed on Sep. 29, 2010.

(30) Foreign Application Priority Data

Sep. 29, 2010 (GB) .................................. 1016332.7

(51) Int. Cl.
*A61L 2/16* (2006.01)
(52) U.S. Cl.
USPC ................ 422/28; 422/37; 134/84; 134/94.1; 134/99.1
(58) Field of Classification Search
USPC ......... 422/28, 37; 424/1.13; 134/26, 84, 94.1, 134/99.1
See application file for complete search history.

(56) References Cited

U.S. PATENT DOCUMENTS

| 5,152,461 A | 10/1992 | Proctor |
| 5,616,347 A | 4/1997 | Alliger et al. |
| 6,387,384 B1 | 5/2002 | Probert et al. |

FOREIGN PATENT DOCUMENTS

| EP | 0 287 074 | 10/1988 |
| GB | 2 422 545 | 8/2006 |
| JP | 58-13507 | 1/1983 |
| JP | 3-52802 | 3/1991 |
| JP | 2002-119582 | 4/2002 |
| WO | WO 85/04107 | 9/1985 |
| WO | WO 2005/011756 | 2/2005 |
| WO | WO 2006/079822 | 8/2006 |
| WO | WO 2010/133855 | 11/2010 |

OTHER PUBLICATIONS

International Search Report for International Application No. PCT/GB2011/051768 mailed Mar. 13, 2012.
International Preliminary Report on Patentability for International Application No. PCT/GB2011/051768 mailed Oct. 9, 2012.

*Primary Examiner* — Sean E Conley
(74) *Attorney, Agent, or Firm* — Merchant & Gould P.C.

(57) ABSTRACT

A hand sanitizer (2) comprises: (a) a first part (14) comprising a chlorite solution and contained in a first dispenser (4) whereby it will be dispensed as a spray or jet of liquid; and (b) a second part (16) comprising an acid solution and contained in a second dispenser (6) whereby it will be dispensed as a second spray or jet of liquid; wherein the chlorite and the acid will react to provide chlorine dioxide when the first part is mixed with the second part; and wherein a mixture (18) of equal quantities of the first part and the second part contains at least 15% alcohol by weight; and wherein at least a part of the alcohol comprises 3-methoxy-3-methylbutan-1-ol (MMB).

21 Claims, 3 Drawing Sheets

HAND SANITIZER

This application is a National Stage Application of PCT/GB2011/051768, filed 20 Sep. 2011, which claims benefit of Ser. No. 61/387,729, filed 29 Sep. 2010 in the United States of America, and Serial No. 1016332.7, filed 29 Sep. 2010 in Great Britain and which applications are incorporated herein by reference. To the extent appropriate, a claim of priority is made to each of the above disclosed applications.

BACKGROUND

The present invention relates to a hand sanitizer.

The rise of hospital-acquired infections such as MRSA and *Clostridium difficile* has emphasized the need for cleanliness. In particular, effective hand sanitizing is needed for people working in a clinical environment.

SUMMARY OF THE INVENTION

Aspects of the invention are specified in the independent claims. Preferred features are specified in the dependent claims.

The invention provides the benefits of an antibacterial alcohol hand wash and sanitizer with the sporicidal properties of chlorine dioxide ($ClO_2$).

The alcohol is or contains 3-methoxy-3-methylbutan-1-ol (MMB) which we have found to provide fast drying times and improved skin feel compared to ethanol. Other alcohols may optionally be included, notably ethanol, isopropanol, n-propanol or a mixture of these.

We have surprisingly found that producing $ClO_2$ in an the presence of a substantial quantity of an alcohol does not noticeably result in disagreeable oxidized products of the alcohol, such as acetaldehyde or acetic acid from ethanol. Without wishing to be bound by theory, we believe that the short time during which the $ClO_2$ is in contact with the alcohol when the liquids are mixed does not allow oxidation of the alcohol to a level where the smell of oxidized product is noticeable. Moreover, we have surprisingly found that sodium chlorite is stable in an alcoholic medium for extended periods, despite its being an oxidizing agent.

The dispenser may be a conventional trigger-operated pump or sprayer in which the contents are expelled manually by operation of the trigger by the user. Alternatively, the dispenser may contain a propellant to dispense the contents when operation of the trigger opens a valve. Suitable dispensers will be well known to those skilled in the art.

In a preferred embodiment, the first dispenser and the second dispenser are connected together or provided in a common housing. Preferably, both parts are dispensed simultaneously by operation of a single trigger or other actuator. A dual dispenser such as described in U.S. Pat. No. 5,152,461 may be used to dispense the two parts. The dispenser consists of two pump systems, with a single trigger operating both chambers. It is a mechanical dispenser which dispenses the two components simultaneously in a precise and fixed ratio. The first part and the second part are kept separate until the moment of application. Alternatively, a touchless dispenser may be used, which automatically dispenses a dual spray or jet of liquid or gel when a user's hands are detected to be in a suitable position.

The first and second parts are each dispensed as a spray of droplets or a jet of liquid, followed by mixing on the user's hands. To facilitate manipulation on the hands, and cling to the hands, each liquid may optionally be thickened or gelled to provide a more viscous liquid. For convenience the term 'liquid' is used herein to include gels.

Suitable gelling agents will be well known to those skilled in the art. Non-limiting examples include hydroxyalkylcelluloses, notably hydroxyethylcellulose or hydroxypropylcellulose, gelatine, poly(vinyl alcohol), alginates, carboxymethylcellulose, carrageenan, guar gum, gum agar, gum Arabic, gum ghatti, gum karaya, gum tragacanth, locust bean gum, pectins, polyacrylamide, polyacrylic acid and its homologues, polyethylene glycol, poly(vinyl pyrrolidone), starch and modified starches, tamarind gum, xanthan gum. The gelling agents are selected to provide a stable gel structure of a desired viscosity. The gelling agent may comprise from about 0.1 to 5% by weight of each part, notably from about 0.5 to 3%, preferably from about 1 to 2%.

In a preferred embodiment, a humectant is included in at least one of the first and second parts, preferably in both parts. Humectants serve to reduce the rate of evaporation of components and improve product feel if direct skin contact is involved. We have found that the use of a humectant reduces the volatility of chlorine dioxide, which reduces the odour of chlorine dioxide and prolongs the life of the activated mixture. Non-limiting examples of suitable humectants include sodium lactate and polyols, for example glycerine, sorbitol, propylene glycol, diethylene glycol and ethylene glycol. The humectant may be present in any desired amount, particularly from about 0.1 to 50% by weight, notably from about 0.5 to 10%, preferably from about 1 to 3%.

BRIEF DESCRIPTION OF THE DRAWINGS

The invention will now be further described, by way of example only, with reference to the following drawings in which.

DETAILED DESCRIPTION

In this specification, all parts are by weight unless otherwise indicated.

Figure 1:
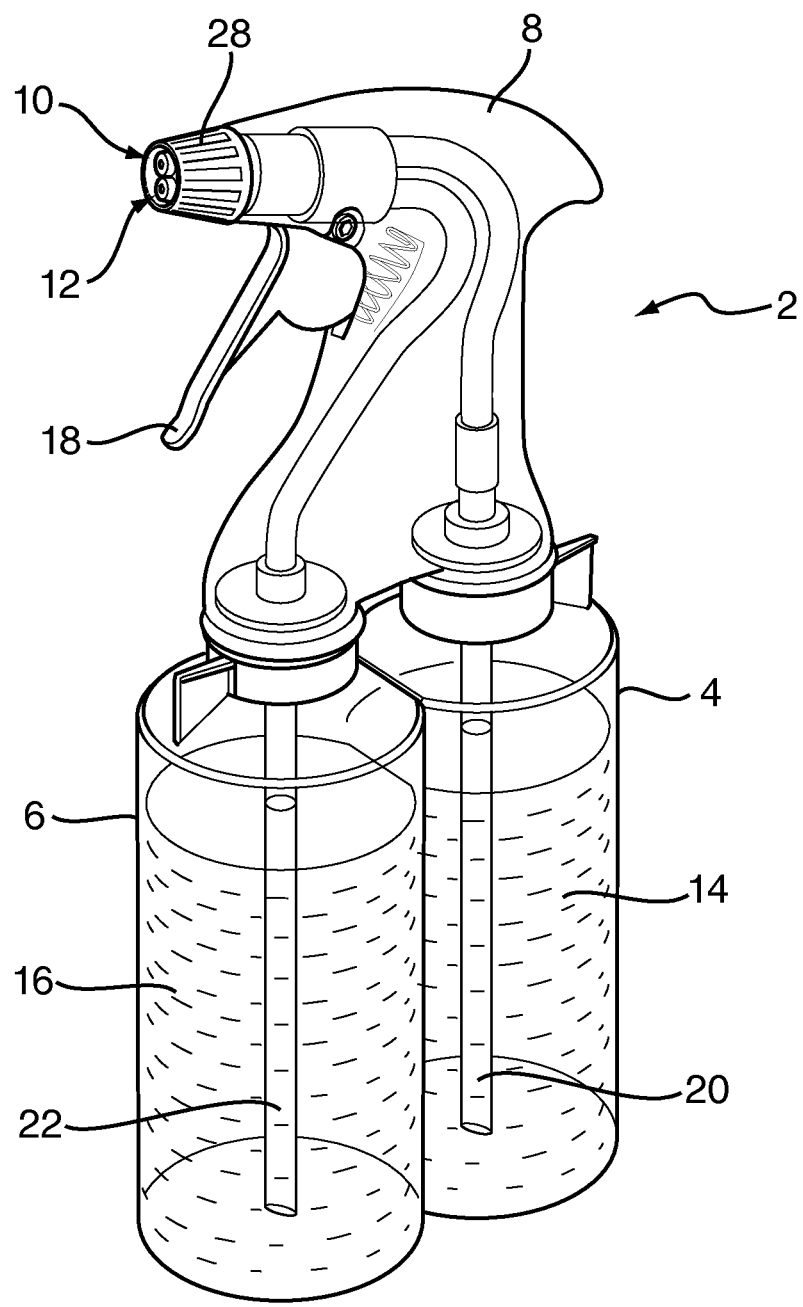
FIG. 1 shows a hand sanitizer in accordance with an embodiment of the invention.

The hand sanitizer 2 shown in FIG. 1 is a dual dispenser having a first dispenser chamber 4 and a second dispenser chamber 6. The first chamber 4 contains a first part 14 comprising a chlorite in an aqueous alcoholic solution, and the second chamber 6 contains a second part 16 comprising an acid mixture in an aqueous alcoholic solution. The chambers 4, 6 are part of two pump systems which dispense their contents via respective dip tubes 20,22 through nozzles 10,12 in a common housing 8 to which each chamber 4,6 is releasably secured. Operation of a single trigger 18 causes a volume of liquid to be pumped from each chamber 4, 6 simultaneously via the dip tubes 20,22 and nozzles 10,12. The nozzles 10,12 are housed in an adjustable nozzle head 28 which may be rotated to adjust the liquid output between a jet and a spray of liquid or gel droplets. The dispensing mechanism is described in detail in U.S. Pat. No. 5,152,461 and U.S. Pat. No. 5,332,157, the contents of which are incorporated herein by reference in their entirety.

In the present example, the first part 14 is made up to the formulation of Table 1. The second part 16 is made up to the formulation of Table 2.

The first part and the second part are miscible to produce $ClO_2$. However, they are kept separate from each other until the point of dispensing, thereby ensuring that $ClO_2$ is formed only within a mixture of the liquids.

TABLE 1

| First Part | | % |
|---|---|---|
| 1 | Demineralized water | Balance |
| 2 | Sodium chlorite solution (25%) | 2.00 |
| 3 | 3-Methoxy-3-methylbutan-1-ol (MMB) | 25.00 |

TABLE 2

| Second Part | | % |
|---|---|---|
| 1 | Demineralized water | Balance |
| 2 | 3-Methoxy-3-methybutan-1-ol (MMB) | 25.00 |
| 3 | Citric acid (ANH) | 0.80 |
| 4 | Sorbic acid | 0.10 |
| 5 | Boric acid | 0.10 |
| 6 | Glycerine | 0.15 |
| 7 | PEG-8 Dimethicone, PEG-8 Ricinoleate Zenicone XX (emollient) | 0.50 |
| 8 | Colour | As required |

Figure 2:
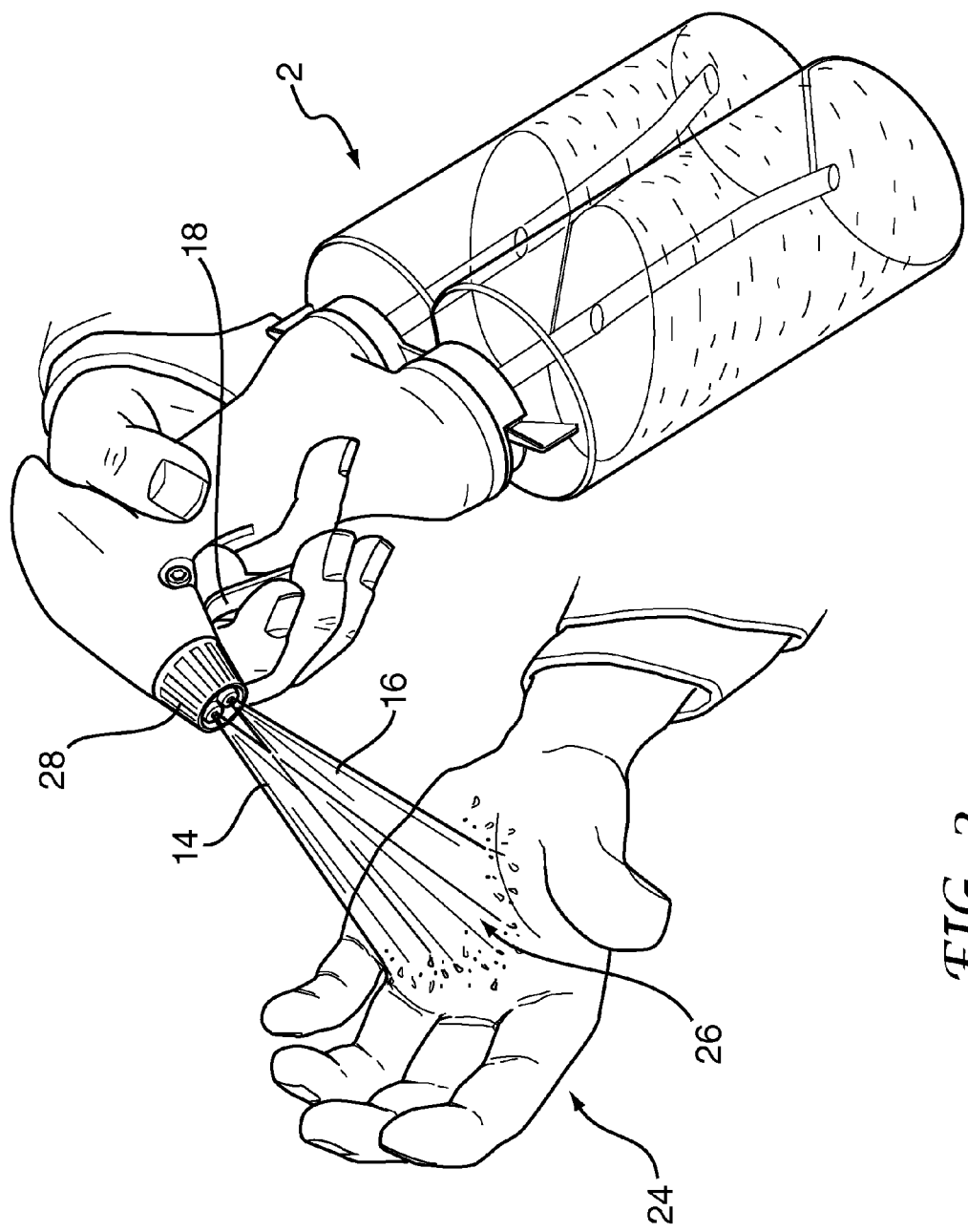
FIG. 2 shows the hand sanitizer of FIG. 1 in use.

Referring now to FIG. 2, the liquid from each nozzle is sprayed onto a user's hand 24 as a spray of droplets, or a jet, by the action of a user's finger on the trigger 18. The liquids mix to provide a sterilizing composition 26 containing an alcohol (in this example, MMB) and $ClO_2$. The user rubs both hands together to mix the liquids thoroughly and cover his hands with the sanitizing composition 26.

Figure 3:
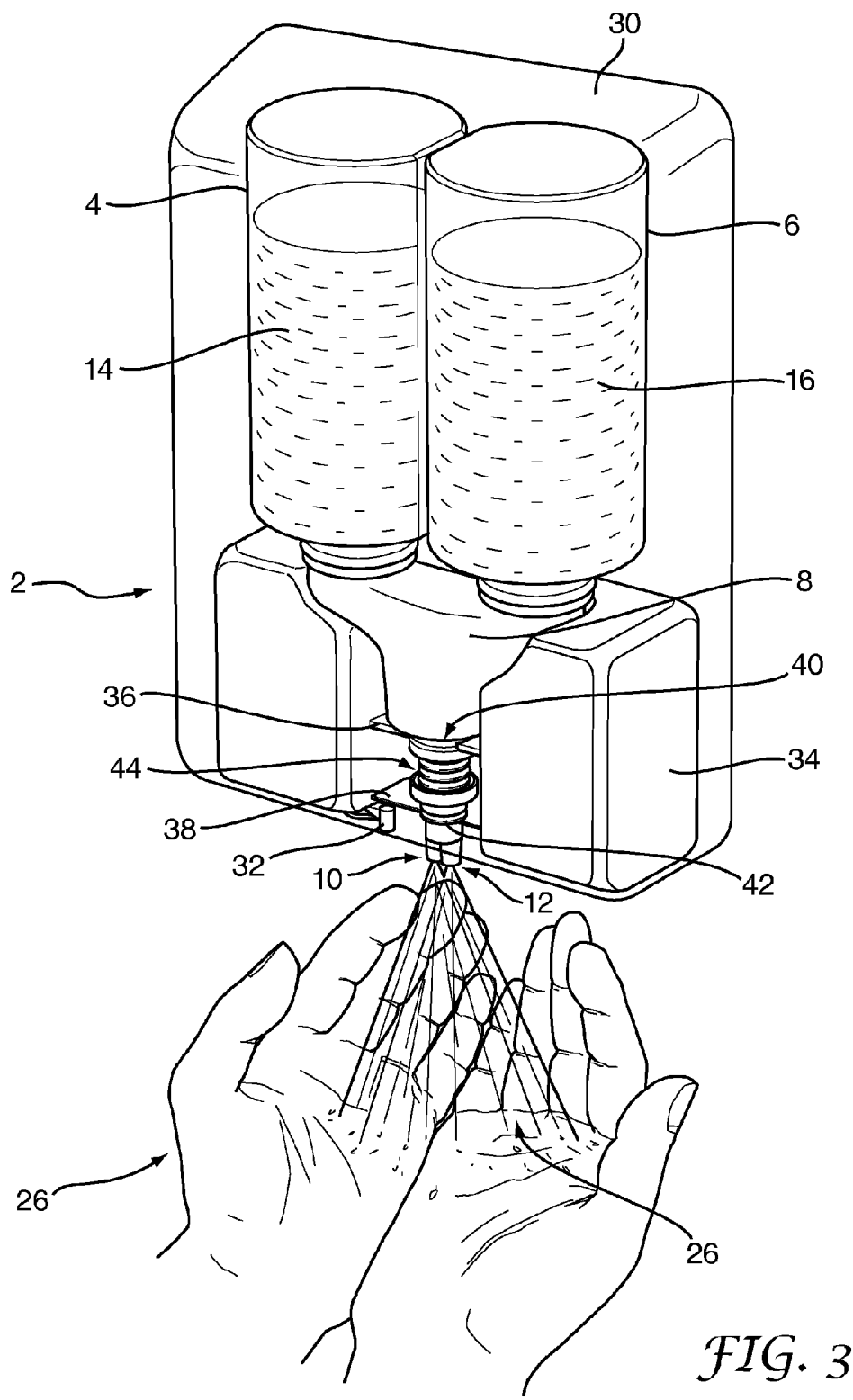
FIG. 3 shows a hand sanitizer in accordance with another embodiment of the invention.

In the embodiment illustrated in FIG. 3, the hand sanitizer 2 is a touchless dual dispenser provided in a wall-mounted cabinet 30. The first chamber 4 and second chamber 6 are connected to corresponding nozzles 10,12 via separate tubing within a common housing 8. The cabinet 30 has a housing 34 in which are mounted electrical components (not shown) including a battery, a motor and a control unit linked to a proximity sensor 32 at the bottom of the cabinet 30.

In use, the common housing 8 is disposed within an opening in the housing 34, and secured by an upper jaw member 36 and a lower jaw member 38 which engage with corresponding features 40, 42 on a dispensing mechanism 44. In this example, the lower jaw member 38 is operably connected to the motor (not shown). When the proximity sensor 32 detects a user's hands 24 under the nozzles 32,34, the control unit actuates the motor to lift the lower jaw member 38, which in turn lifts the engaging feature 42 and causes the first part 14 and second part 16 to be simultaneously dispensed as a spray of fine droplets of liquid. The sprays mix to form the sanitizing composition 26 on the user's hands 24, and the user rubs both hands together to mix the liquids thoroughly and cover both hands with the sanitizing composition 26.

After the user's hands have been thoroughly sanitized by covering and rubbing with the mixture 26, the user may rinse off the mixture 26. However, the alcohol content makes the mixture quite volatile and the user may choose simply to allow his hands to dry by evaporation.

Antibiotics, antivirals, or other antimicrobial agents may optionally be incorporated in either or both of the first part and the second part. Suitable agents will be well known to those of ordinary skill in the art. Examples include cationics, amphoterics and phenolics.

Humectants, moisturizers and fragrances may optionally be included in the first part or (preferably) the second part, as is well known in the art per se.

Corrosion inhibitors may be included in the first part and/or the second part, for improved packaging and protection of the dispenser.

The embodiment of Table 1 provides liquids which contain 25% alcohol and, when combined, chlorine dioxide, which we have found provides excellent sterilizing properties when used as a hand sanitizer.

The embodiment of Table 1 was tested for effectiveness against a range of micro-organisms using a method in accordance with EN 13727. Results are given in Table 3.

TABLE 3

| | | | Result | |
|---|---|---|---|---|
| Organism | Specification (Log reduction) | Contact time | Log reduction dirty conditions | Pass/Fail |
| Staphylococcus aureus ATCC 6538 | ≥5 | 30 sec | >5.27 | Pass |
| | | 60 sec | >5.27 | Pass |
| Pseudomonas aeruginosa ATCC 15442 | ≥5 | 30 sec | >5.30 | Pass |
| | | 60 sec | >5.30 | Pass |
| Enterococcus hirae NCIMB 8192 | ≥5 | 30 sec | >5.25 | Pass |
| | | 60 sec | >5.25 | Pass |
| Escherichia coli NCTC 10538 | ≥5 | 30 sec | >5.03 | Pass |
| | | 60 sec | >5.03 | Pass |

We have found that use of MMB as some or all of the alcohol component can provide the benefits of fast drying and greatly improved skin feel compared to ethanol. MMB also has the benefit over ethanol that it is substantially non-flammable. Pure MMB has a flash point of 68° C. measured by Tag Closed Cup, while a mixture of MMB and 10% or more water has no flash point. MMB is considered to be extremely safe, having no R and S phrases and Occupational Exposure Limit.

Table 4 summarises comparative drying speeds of mixtures of MMB and water, and mixtures of ethanol and water. In each case, a 0.1 ml sample was visually assessed for speed of drying. Rates of evaporation were determined by placing a sample onto a standard filter paper and measuring the time for complete evaporation. The time for diethyl ether evaporation is taken as unity, and the quoted numbers for each sample are expressed relative to diethyl ether.

TABLE 4

| Demin. Water (D) | 10% Ethanol in D. | 50% Ethanol in D. | 10% MMB in D. | 50% MMB in D. |
|---|---|---|---|---|
| 77 | 21 | 12 | 24 | 14 |

The above demonstrates a similar evaporation rate for comparable solutions of ethanol in water and MMB in water. Qualitative testing demonstrated a greatly improved skin feel of MMB over ethanol.

Although MMB is used because of its very low flammability and good skin feel, other alcohols such as ethanol, propanol or isopropanol may also be used in the formulation in combination with MMB. We have surprisingly found that producing $ClO_2$ in the presence of a substantial quantity of an alcohol does not noticeably result in disagreeable oxidized products of the alcohol, such as acetaldehyde or acetic acid from ethanol. Without wishing to be bound by theory, we believe that the short time during which the $ClO_2$ is in contact with the alcohol when the liquids are mixed does not allow oxidation of the alcohol to a level where the smell of oxidized product is noticeable. Moreover, we have surprisingly found that sodium chlorite is stable in an alcoholic medium containing up to 80% ethanol for extended periods, despite its being an oxidizing agent. Accordingly, the invention can provide a hand sanitizer which dispenses liquid or gel components that provide the germicidal benefits of both $ClO_2$ and alcohol.

We investigated a number of additives for incorporation in the acidic phase (Table 2) to reduce potential skin irritation caused by repetitive use of the formulation. The additives investigated were:
1. Cetyl Triethylmonium Dimethicone Copolyol Olivate
2. Sunfloweramidopropyl Trimethyl Ammonium Chloride PEG-8 Dimethicone Succinate
3. *Calendula Officinialis* Extract
4. Methylsilanol Mannuronate
5. Silanediol Salicylate
6. Meadowfoam Delta Lactone (*Limnanthes Alba*)

Each additive was included in the formulation of Table 2 at between 1% and 5% by weight. Trials demonstrated that additive 6), Meadowfoam delta-lactone was most effective.

Irritation Protocol

Using the acid phase of Table 2, a cotton wool pad was wetted and applied to a 3 cm area on the inside of both forearms of the volunteer subjects. Reaction to the application was monitored by noting the time when there was a sensation of irritation. Results are given in Table 5.

TABLE 5

| Basic Formulation | Per Table 2 | Per Table 2 | Per Table 2 |
|---|---|---|---|
| Wt % Meadowfoam delta-lactone | 0% | 2.5% | 5% |
| First signs of irritation | 7.3 minutes | 22.0 minutes | No irritation at any time |
| % of participants with irritation | 100 | 50 | 0 |

While this test does not specifically measure anti-irritancy with respect to reducing irritation caused by an applied insult, it clearly demonstrates that Meadowfoam delta-lactone provides an effective anti-irritation performance in at least some subjects.

It will be understood that, since the chlorite and the acid liquids will be mixed on application to a user's hands, the anti-irritant agent may be contained in either or both of the liquid phases.

The invention claimed is:

1. A hand sanitizer comprising:
   (a) a first part comprising a chlorite solution and contained in a first dispenser whereby it will be dispensed as a first spray or jet of liquid; and
   (b) a second part comprising an acid solution and contained in a second dispenser whereby it will be dispensed as a second spray or jet of liquid;
      wherein the chlorite and the acid will react to provide chlorine dioxide when the first part is mixed with the second part; and wherein a mixture of equal quantities of the first part and the second part contains at least 15% alcohol by weight; and wherein
      at least a part of the alcohol comprises 3-methoxy-3-methylbutan-1-ol (MMB).

2. A hand sanitizer according to claim 1, wherein the first part and the second part each further comprises from 0.01 to 1% by weight of a thickener.

3. A hand sanitizer according to claim 2, wherein the thickener is present in a concentration of from 0.1 to 0.25% by weight.

4. A hand sanitizer according to claim 1, wherein the first part and the second part each further comprises a gelling agent whereby the aqueous media are each in the form of a gel.

5. A hand sanitizer according to claim 1, wherein each of the first part and the second part contains at least 15% alcohol by weight.

6. A hand sanitizer according to claim 1, wherein the alcohol is present in a concentration of from 20-80% by weight when equal quantities of the first part and the second part are mixed.

7. A hand sanitizer according to claim 1, wherein the alcohol is present in a concentration of from 25-50% by weight when equal quantities of the first part and the second part are mixed.

8. A hand sanitizer according to claim 1, wherein substantially all of the alcohol is MMB.

9. A hand sanitizer according to claim 1, wherein at least one of the said solutions further comprises an anti-irritant agent selected from the group consisting of Cetyl Triethylmonium Dimethicone Copolyol Olivate, Sunfloweramidopropyl Trimethyl Ammonium Chloride PEG-8 Dimethicone Succinate, *Calendula Officinialis* Extract Methylsilanol Mannuronate, Silanediol Salicylate, Meadowfoam Delta Lactone (*Limnanthes Alba*), and mixtures of any two or more of the foregoing.

10. A hand sanitizer according to claim 9, wherein the anti-irritant agent comprises Meadowfoam delta-lactone.

11. A hand sanitizer according to claim 9, wherein the anti-irritant agent is in the acid solution.

12. A hand sanitizer comprising:
   (a) a first part comprising a chlorite in a gel and contained in a first dispenser whereby it will be dispensed as a first spray or jet of gel; and
   (b) a second part which comprises an acid in a gel and contained in a second dispenser whereby it will be dispensed as a second spray or jet of gel;
      wherein the chlorite and the acid will react to provide chlorine dioxide when the first part is mixed with the second part; and wherein a mixture of equal quantities of the first part and the second part contains at least 15% alcohol by weight; and wherein
      at least a part of the alcohol comprises 3-methoxy-3-methylbutan-1-ol (MMB).

13. A hand sanitizer according to claim 12, wherein each of the first part and the second part contains at least 15% alcohol by weight.

14. A hand sanitizer according to claim 12, wherein the alcohol is present in a concentration of from 20-80% by weight when equal quantities of the first part and the second part are mixed.

15. A hand sanitizer according to claim 12, wherein the alcohol is present in a concentration of from 25-50% by weight when equal quantities of the first part and the second part are mixed.

16. A hand sanitizer according to claim 12, wherein substantially all of the alcohol is MMB.

17. A hand sanitizer according to claim 12, wherein at least one of the said solutions further comprises an anti-irritant agent selected from the group consisting of Cetyl Triethylmonium Dimethicone Copolyol Olivate, Sunfloweramidopropyl Trimethyl Ammonium Chloride PEG-8 Dimethicone Succinate, *Calendula Officinialis* Extract Methylsilanol Mannuronate, Silanediol Salicylate, Meadowfoam Delta Lactone (*Limnanthes Alba*), and mixtures of any two or more of the foregoing.

18. A hand sanitizer according to claim 17, wherein the anti-irritant agent comprises Meadowfoam delta-lactone.

19. A hand sanitizer according to claim 17, wherein the anti-irritant agent is in the acid solution.

20. A method of sanitizing hands, comprising taking a hand sanitizer according to claim 1, dispensing some of the first part and some of the second part onto a user's hand, and rubbing the user's hands together so as to mix the two parts and cover the user's hands with the resulting mixture.

21. A method of sanitizing hands, comprising taking a hand sanitizer according to claim 12, dispensing some of the first part and some of the second part onto a user's hand, and rubbing the user's hands together so as to mix the two parts and cover the user's hands with the resulting mixture.

* * * * *